United States Patent
Fox

(12) 
(10) Patent No.: US 6,344,599 B1
(45) Date of Patent: Feb. 5, 2002

(54) OPEN POLLINATED HYBRID AND THE METHOD OF PRODUCING

(75) Inventor: Gregory J. Fox, Fargo, ND (US)

(73) Assignee: Barkley Seed, Inc., Yunma, AZ (US)

( * ) Notice: Subject to any disclaimer, the term of this patent is extended or adjusted under 35 U.S.C. 154(b) by 0 days.

(21) Appl. No.: 09/168,070

(22) Filed: Oct. 8, 1998

Related U.S. Application Data

(60) Provisional application No. 60/061,448, filed on Oct. 8, 1997.

(51) Int. Cl.$^7$ ............................ A01H 1/00; A01H 1/02
(52) U.S. Cl. ............... 800/275; 800/320.1; 800/260
(58) Field of Search ................. 800/230.1, 320, 800/260, 275

(56) References Cited

U.S. PATENT DOCUMENTS 5,706,603 A    1/1998  Bergquist et al. ............ 47/58
5,763,756 A    6/1998  Bergquist .................... 800/200

OTHER PUBLICATIONS

W. R. Fehr. Principles of Cultivar Development, McGraw–Hill,Inc. p. 117, 1987.*

F.N. Briggs et al. Introduction to Plant Breeding, Reinhold Books . . . p. 255, 1967.*

Hayes, H.K., et al., "The Development of a Synthetic Variety of Corn from Inbred Lines," 1944, pp. 998–1001, *J. of the Am Soc. of Agronomy* (Abstract of article).

Hayes, H.K., "Present–Day Problems of Corn Breeding," 1926, pp. 344–363, *J. of the Am. Soc. of Agronomy*.

* cited by examiner

*Primary Examiner*—Gary Benzion

(57) ABSTRACT

The present invention is directed to an open pollinated hybrid with yields similar to standard $F_1$ hybrids and to methods of producing open pollinated hybrids. This invention results in a method of inexpensive, continuous seed increase with minimal loss of hybrid vigor.

28 Claims, No Drawings

OPEN POLLINATED HYBRID AND THE METHOD OF PRODUCING

Cross Reference

This application is a conversion from a provisional and claims priority from U.S. Provisional Application Serial No. 60/061,448 filed Oct. 8, 1997.

BACKGROUND OF THE INVENTION

The present invention relates to a method of producing an open pollinated hybrid and to open pollinated hybrids of corn and sunflowers.

The publications and other materials used herein to illuminate the background of the invention or provide additional details respecting the practice, are incorporated by reference, and for convenience are respectively grouped in the appended List of References.

Domestic (cultivated) corn is primarily a creation of prehistoric Native North American breeders. Selection was carried out on corn producing a vast array of varieties and types of corn. Maturities ranged from 60 days to maturity to 160 days to maturity. Grain hardness ranged from soft floury to hard flinty. Grain color ranged from deep purple to pale white with all the shades in between. Since corn is a cross pollinated plant type, the Native American breeders made selections of material plant types with no control of the pollen (male) parent. This type of selection is called half sib selection. Thus, corn was developed as an open pollinated crop, spread across North America, with numerous local varieties adapted to local conditions. All of the commercially grown corn, world wide, is derived from this North American germplasm pool.

The European colonists that came to the New World (North America) used the Native American open-pollinated varieties as they found them and continued the method of half sib selection to improve yield and agronomic qualities. This method of breeding continued into the 20th Century with the local varieties across North America representing separate gene pools based on the original Native American open pollinated varieties. The type of grain preferred by colonial breeders was a medium textured seed of yellow color with a flinty outer endosperm enclosing an inner soft floury endosperm. As drydown progresses the soft endosperm collapses and an indentation is formed on the crown of the corn kernel, thus the name "yellow dent" was applied to this type of corn grain. Yellow dent corn is the predominant version of the grain that is used worldwide for food, feed and fuel.

At the beginning of the 20th Century, genetic researchers began to self-pollinate corn. Selfing used bags over the ears and the silks to control the flow of pollen from the tassel to the silks of individual plants. Successive generations of self pollinating (selfing) resulted in a continuing loss of vigor with plants becoming weaker and less able to produce seed in quantity. To those skilled in the art this phenomena is known as "inbreeding depression". It is also well known to those skilled in the art that when weak unrelated inbreds were crossed, the resultant progeny (seed) gave rise to plants that were many times more vigorous and higher yielding than the parents. This phenomena is known as "hybrid vigor"; the progeny seed is known as hybrid ($F_1$) seed.

While it was possible to produce hybrid vigor with reference to weak inbred lines, it was not initially apparent when inbreds were derived from one of the accepted commercial open pollinated varieties and the standard for yield and vigor was such a commercial variety. However after much trial and error research it was discovered that when inbreds were selected from a range of the adapted open pollinated varieties from widely divergent geographic areas that hybrids were produced that yielded far more than the open pollinated varietal parents with a far more uniform population of plants. It became clear that certain varieties when crossed together yielded commercial grade hybrid vigor, but most did not. The special populations (open pollinated varieties) that produced hybrid vigor when combined were called heterotic groups. The major heterotic groups are listed in Table 1:

TABLE 1

| Variety | | Origin |
| --- | --- | --- |
| Lancaster Surecrops | (C103) | Connecticut |
| Canadian Morden | (CMV3) | Canada |
| Early Butler | (CO109) | New York |
| High Yield | (HY) | Illinois |
| Ohio 43 | (OH43) | Ohio |
| Reid Yellow Dent | (SSS) | Iowa |
| Wisconsin 153 | (W153) | Wisconsin |
| Wilson Farm Reid 9 | (WF9) | Indiana |

As an example, it was found that when inbreds derived from Reid Yellow Dent were crossed with inbreds from Lancaster Surecrop produced hybrids that far out-yielded any commercial open pollinated variety. From this process/product the hybrid seed corn industry began. The first hybrids became available in the 1930s and by the late 1950s virtually all of the open pollinated corn varieties had been replaced by hybrids.

The actual mechanism of hybrid vigor is still poorly understood, with the result that genetic improvement has been confined to breeding and selection within the heterotic groups. Thus one can improve the stalk strength and yield of C103 but the basic genetic background of C103 must be maintained so that the hybrid relationship with Stiff Stalk Synthetic (SSS) is maintained. This results in a cumbersome breeding process in which improved lines must always be evaluated in reference to specific heterotic mates. For example an improved line from C103 can be produced but if it fails to yield hybrid vigor with SSS it is discarded. Therefore, hybrid breeding is an expensive process.

The actual production of hybrid seed is also an expensive process. In a production field two inbred parents are planted. One is a female plant upon which the hybrid seed will be produced. This plant must be detasselled prior to pollination or genetically male sterilized. The second plant is a male pollen parent used to pollinate the female plant. The seed of this male plant is not harvested for hybrid seed. Thus to produce hybrid seed it is necessary to use weak yielding inbreds as seed producing parents, and to use non-seed producing parents as pollinators. Based on a variety of environmental conditions, the male and female plants may fall out of synchronization with silking and pollination timing resulting in reduced or non-existent seed production. For all the above reasons, hybrid seed production is expensive and somewhat complicated, with the result that hybrid seed production and the resultant hybrid seed is unavailable to many subsistence farmers in developing countries that need it most.

Like corn, sunflower is a crop that was developed by the Native Americans before the arrival of the European explorers and settlers. It was used as a nutritious oily food crop often complementing corn in their diets. It had an additional dimension in that certain selected varieties produced purple, colorant bearing hulls with high levels of anthocyanin pigment. These hulls were used in a boiling water type treatment to color the clothes and blankets of the people. Colors ranged from red to blue depending on the treatment of the hull material (anthocyanins are color sensitive to pH values with low pH levels yielding red colors and higher pH levels yielding blues). The sunflower seed of commerce is an achene, which is a dry fruit with the hard woody hull representing ovary tissue with the kernel representing the ovule (seed). The Native Americans would consume the sunflower as whole achenes (often roasted) or as shelled kernels. The hulls of the sunflower can be any color with black, white, black/white striped and purple being most common. The sunflower traveled from the New World and found its way to Europe where it found special acceptance as a cool climate oil seed crop in Russia. In the first half of the 20th Century under V.S. Pustovoit, a number of widely adapted open pollinated (OP) black hulled oil seed varieties (not hybrids) with oil content greater then 40% were developed. The old Native American land varieties had oil content of about 30%. As with corn, all breeding work on sunflower prior to the development of hybrids was accomplished with half sib selection techniques both in the New World and Russia. Russian OP varieties were introduced into the Northern Great Plains (Minn, N.Dak., S.Dak.) in the 1960s. The OP variety Peredovik was especially successful and widely grown. However, the disuniformity of this OP variety and the lack of stalk strength made the American farmers desire an improved varietal type and hopefully a hybrid type. This was a difficult task because the sunflower is not easily male sterilized as is corn in which tassels are removed. In corn, the male (tassels) and female (silk) organs are at separate positions on the plant. In sunflower, the male and female sex organs are collocated in tiny individual florets (1000 to 3000 per sunflower head). Thus making a sunflower hybrid was a commercial impossibility.

However, in 1969, Dr. Leclerq of France, through interspecific crosses developed a stable and usable cytoplasmic male sterile system (CMS) for sunflower that yielded sunflower plants and thus lines that produced plants that were 100% male sterile. Such plants could serve as females in the production of sunflower hybrids. These types of plants are called A lines and must be maintained (pollinated) by pollen producing equivalent lines called B lines. Thus, each female A line must have an equivalent (identical in appearance) B line (as a pollen donor) in order to maintain the A line (produce seed) since no pollen is produced by the A line. An A line is created by backcrossing the CMS trait into a selected B line parent. In 1970, just one year after Leclerq's discovery of the CMS trait, Dr. Kinman (USDA) and others discovered nuclear genes for fertility restoration in wild sunflower and soon restoration genes were transferred (backcrossed) into branched oil seed and confectionary parental (male) lines called R (restorer lines). These two discoveries made sunflower hybrids a reality by the early 1970s by a process in which a cytoplasmic male sterile (CMS) A line is crossed to a pollen producing restorer (R) line to yield a fully fertile $F_1$ hybrid.

BRIEF SUMMARY OF THE INVENTION

It is an object of the present invention to provide a method for producing high yielding corn and sunflower hybrids without having to produce a new crop of $F_1$ hybrid seed for each growing season. The present invention provides a method to produce open pollinated corn and sunflower hybrids that can be increased by simple isolation techniques therefor eliminating the costly expense of continuous $F_1$ hybrid seed production. The method of the present invention includes crossing inbreds from complementary heterotic groups to yield an $F_1$, hybrid. This $F_1$ hybrid is then selfed for 1 to 5 or more additional generations resulting in the following: $F_2$ (second generation), $F_3$ (third generation), $F_4$ (fourth generation) and $F_5$ (fifth generation) seed. A representative plant and/or plants and/or ear row(s) from the $F_2$, $F_3$, $F_4$ or $F_5$ generations are selected that retain the $F_1$ hybrid characteristics for yield, agronomic qualities and general appearance. These selected $F_2$, $F_3$, $F_4$ and $F_5$'s are grown out in isolation as open pollinated hybrid seed. As long as isolation is maintained, the open pollinated hybrid can be increased in this manner with no loss of hybrid vigor.

DEFINITIONS

In order to provide a better understanding of the specifications and claims contained in this application, definitions of some terms used therein are provided below:

Backcross—As used herein, the term "backcross" means a cross of a hybrid to either of its parents.

Backcross Breeding—As used herein, the term "backcross breeding" means a system of breeding whereby recurrent (repeated) backcrosses are made to one of the parents of a hybrid accompanied by selection for a specific character or characters.

Complementary Heterotic Inbred Lines—As used herein, the term "complementary heterotic inbred lines" means inbred lines, that when crossed, give rise to $F_1$ hybrid s that display heterosis.

Cross pollination—As used herein, the term "cross pollination" means a cross between two different plants.

Field Isolation—As used herein, the term "field isolation" means the separation of one group from another so that mating between or among groups is reduced to a frequency of less than 10%.

$F_1$—As used herein, the term "$F_1$" means the first generation of a cross.

$F_2$—As used herein, the term "$F_2$" means a progeny obtained by self-fertilization of $F_1$ individuals. If selfing is continued the F- level is iterated to reflect the number of selfed generation. Thus, it can proceed from $F_2$ to $F_3$ to $F_4$ to $F_5$, etc. until selfing has ceased.

Heterosis—As used herein, the term "heterosis" means hybrid vigor such that an $F_1$ hybrid falls outside the mean or range of the parents with respect to some character or characters. Usually applied to size, rate of growth, general thriftiness and seed yield.

Hybrid—As used herein, the term "hybrid" means the product of a cross between genetically unlike parents.

Hybrid visor—As used herein, the term "hybrid vigor" means the yield performance of an $F_1$ hybrid exceeds the yield range of the parents.

Heterozygous—As used herein, the term "heterozygous" means having unlike (different) alleles at one or more corresponding loci (opposite of homozygous).

Homozygous—As used herein, the term "homozygous" means having like (the same) alleles at corresponding loci on homologous chromosomes. An organism can be homozygous at one, some, or all loci.

Inbred Line—As used herein, the term "inbred line" means a line produced by inbreeding. As used herein, an inbred line is considered to be any material that has undergone at least one self fertilization and includes $F_2$, $F_3$, $F_4$, $F_5$, $F_6$ and all additional selfing generations.

Initial $F_1$ Hybrid. As used herein, the term "initial $F_1$ hybrid" means the cross between two or more inbred lines.

Isolation—As used herein, the term "isolation" means a separation of one group from another so that mating among or between groups is reduced to a frequency of less than 10%.

Open pollination—As used herein, the term "open pollination" means the natural (uncontrolled) pollination that occurs within a cross pollinated population or variety.

Selection—As used herein, the term "selection" means discrimination among individuals in the number of offspring contributing to the next generation.

Self Fertilization (self pollination)—As used herein, the term "self fertilization (self pollination)" means the fusion of male and female gametes from the same individual. In this application often denoted by the short hand term "selfing".

Selfing Generation line—As used herein, the term "selfing generation line" means a line produced by inbreeding. A "selfing generation line" is any genetic material that has undergone at least one self-fertilization and includes an $F_2$, $F_3$, $F_4$, $F_5$, $F_6$ and all additional selfing generations.

Variety—As used herein, the term "variety" means a group of individuals within a species which are distinct in form or function from other similar arrays of individuals.

DETAILED DESCRIPTION OF THE INVENTION

The method of the present invention involves, in one embodiment, the crossing of two or more inbred lines to produce initial $F_1$ hybrid s. These initial $F_1$, hybrids were selfed for a number of generations to produce new inbreds (or selfing generation lines) that were tested with elite tester lines (potential heterotic counterparts). Unexpectedly, some of the inbred lines ($F_3$, $F_4$ and $F_5$) retained the hybrid vigor of the initial $F_1$, hybrid. When such lines were allowed to open pollinate in isolation, as a population for seed increase, there was little or no loss of hybrid vigor. One preferred embodiment of the method of the present invention is as follows:

1. Heterotic complementary inbred lines are crossed which result in a high yielding $F_1$, hybrid (initial $F_1$ hybrid);
2. This initial $F_1$, hybrid is selfed for 1 to 4 or more generations to produce inbred lines;
3. Selected inbred lines (also called selfing generation lines) are grown in plots, which may be adjacent to the initial $F_1$, hybrid, and are evaluated for general appearance, agronomic quality, seed quality (appearance), general disease resistance, and yield relative to the $F_1$, hybrid; and
4. Inbred lines that equal or exceed the performance of the initial $F_1$, hybrid and have a similar general appearance are selected, advanced and increased in isolation as an open pollinated hybrid.
5. Seed is further increased by simply repeating step 4 as needed.

The selfing process needed to produce inbred lines for this invention can generally be achieved after about four generations but any number of selfing generations can be used. Since selfing is an expensive and time consuming procedure it is desirable to complete this phase of the process as quickly as possible. However inbred lines of the present invention can be selected after any number of selfing generations, and often it just isn't necessary to go beyond the $F_5$ generation to select these lines.

The method of the present invention involves a breeding technique in which the hybrid vigor trait is fixed in the selfed lines and maintained in isolated cross pollinating production fields. This method has never been described or accomplished prior to this application. The end product of this process, an open pollinated corn hybrid having excellent yield has never been described or previously accomplished.

EXAMPLES

The present invention is further detailed in the following examples which are offered by way of illustration and are not intended to limit the invention in any manner. Standard techniques well known in the art or the techniques specifically described below are utilized.

Example 1

Complementary heterotic inbred lines CM105 (Reid Yellow Dent—SSS type) and CO109 were crossed to produce a 78 day (about 78 days from planting to maturity) $F_1$ hybrid. The initial $F_1$ hybrid was selfed for three generations yielding $F_2$, $F_3$ and $F_4$ seed. Each selfed generation was planted adjacent to the $F_1$ hybrid and only those plants that matched the hybrid for agronomic traits such as height, stalk strength, ear height, ear diameter, rows of seed per ear, number of seeds per row, size and shape of seed, silking and tasseling date, leaf length and width, stalk and leaf color, general disease reaction, final dry down date, final seed yield, and bulk density of harvested seed (test weight) were selfed and advanced to the next generation. After successive generations of selfing, a single $F_4$ plant was selected that closely matched the initial $F_1$ hybrid. The seed was further advanced in isolation as an open pollinated hybrid. This seed produced uniform plant types that match the said $F_1$, hybrid. When grown in plots adjacent to the $F_1$ hybrid, the open pollinated variety is similar to the $F_1$ hybrid for seed yield and appearance.

Example 2

Complementary heterotic inbred lines CM105 (Reid Yellow Dent—SSS type) and A554 (Wilson Farm Reid—WF9 type) were crossed to produce an $F_1$ hybrid of about the 84 day maturity class. The initial $F_1$ hybrid was selfed to yield $F_2$ seed. This seed was planted and a single $F_2$ plant was selected that were similar to the initial $F_1$ hybrid for the agronomic traits such as height, stalk strength, ear height, ear diameter, rows of seed per ear, number of seeds per row, size and shape of seed, silking and tasseling date, leaf length and width, stalk and leaf color, general disease reaction, final dry down date, final seed yield and bulk density of harvested seed (test weight). The selected $F_2$ plant was selfed and the resultant seed was planted and six $F_3$ plants similar to the initial $F_1$ hybrid were selected, selfed, bulked and advanced in isolation as an open pollinated hybrid producing a uniform plant population matching the initial $F_1$, hybrid. When grown in plots adjacent to the initial $F_1$ hybrid the open pollinated hybrid was similar to the initial $F_1$ hybrid for seed yield and appearance.

Example 3

Complementary heterotic inbred lines CM105 (Reid Yellow Dent—SSS type) and W153 were crossed to produce an $F_1$ hybrid of about the 90 day maturity class. The initial $F_1$ hybrid was selfed to yield $F_2$ seed. This $F_2$ seed was planted and 10 plants similar to the initial $F_1$ hybrid were selected and selfed, yielding $F_3$ seed. The $F_3$ seed was planted as ear rows (each planted row was derived from a single $F_3$ ear of corn). One of the ten $F_3$ selections closely matched the $F_1$ hybrid and five random plants from that row were selfed, yielding $F_4$ seed. The $F_4$ seed was planted as five separate ear rows. A single ear row is selected as the closest match to the $F_1$ hybrid and 10 plants from that ear row are randomly selfed, harvested, and bulked as $F_5$ seed, and advanced in isolation as an open pollinated variety producing plant types that match the initial $F_1$ hybrid. When grown in plots adjacent to the initial $F_1$ hybrid, this open pollinated variety was similar to the initial $F_1$ hybrid for seed yield and appearance.

Example 4

Complementary heterotic inbred lines A641 (Reid Yellow Dent—SSS type) and M017 (Lancaster Surecrop—C103 type) were crossed to produce an $F_1$ hybrid of about the 95 day maturity class. The initial $F_1$ hybrid was selfed to produce $F_2$ seed, random ears were selfed through the $F_4$ seed generation and the resultant $F_4$ seed was bulked as a breeding population and grown in isolation and allowed to open pollinate. A single plant from this population was selected as a close match to the initial $F_1$ hybrid and seed was harvested. This seed is further advanced in isolation as an open pollinated hybrid. It produces uniform plant types that match the initial $F_1$ hybrid. When grown in plots adjacent to the initial $F_1$ hybrid this open pollinated hybrid matches the initial $F_1$ hybrid for seed yield and appearance.

Example 5

The production of an open pollinated sunflower hybrid, is accomplished in the same manner as described in the corn examples 1 through 4. Several examples of open pollinated sunflower hybrids produced by the methods described herein will be submitted for illustrative purposes.

Complementary heterotic inbred lines HA821A× RHA801 R were crossed to produce a short statured and semi-erect headed $F_1$ oil seed (oil content greater than 40% on a dry weight basis) hybrid. The $F_1$ hybrid was selfed for three generations yielding $F_2$, $F_3$ and $F_4$ seed. Each selfed generation was planted next to the $F_1$ hybrid and only those plants that matched the hybrid for agronomic traits such as flowering date, height, stalk strength, general disease reaction, leaf size, leaf shape, plant color (shade of green), head shape (concave to convex), number of seeds per head, head orientation (erect to lax), seed shape, seed color (oil seed have a black or gray on black striping pattern; confectionary seed have a black or brown on white striping pattern), hull thickness (confection's are thick, oilseed's are thin), yield, bulk density (test weight) and oil content. Another selection criterion which was included and is unique to sunflower hybrids is male fertility. Since the hybrids are produced using a CMS system, in the $F_2$, $F_3$ and succeeding generations, some male sterile plants are produced and all plants have the CMS cytoplasm. Only those plants with CMS, Rf Rf, that have the fertility restoration gene (Rf Rf) in the homozygous condition are selected for advancement. After successive generations of selfing, a single $F_3$ plant was selected which closely matched the $F_1$ hybrid. The seed was further advanced in isolation as an open pollinated hybrid. This seed produced visually uniform plant types that closely match the said $F_1$ hybrid for seed yield and appearance.

Example 6

Complementary heterotic inbred lines HA821A×HA89B were crossed to yield a single cross CMS female HA821A/HA89B. Since no restoration gene has been incorporated, the resultant hybrid is a total male sterile A line CMS that can be used as a female in the production of a three-way sunflower hybrid in which there are three complementary heterotic parents instead of two. HA821A/HA89B was used as a female in a cross with RHA801R. The resultant $F_1$ three-way hybrid (HA821A/89B x RHA801 R) was selfed for three generations to yield a number of $F_4$ plants that closely resembled the $F_1$ hybrid when evaluated as plants and seed for the traits that were described in Example 5. These $F_4$ plants are bulked to form an open pollinated plant and when grown in isolation, yield plants and seed that closely match the $F_1$ hybrid for seed yield and agronomic appearance.

Example 7

Complementary heterotic inbred line HA821A was crossed with Neagra de Cluj (NDC) B to yield a purple hulled single cross female line HA821A/NDC B. NDC is a purple hulled sunflower line that carries the dominant Tf gene in the homozygous condition (TfTf) for anthocyanin in the hull. Thus, all single cross female plants are purple hulled. This single cross female line is crossed with RHA801 R to yield a three-way hybrid (HA821A/NDC B×RHA801 R) that is segregated for the purple hulled trait. This $F_1$ hybrid was selfed for three generations to yield a number of $F_4$ plants that closely matched the $F_1$ hybrid when the plants and seed were evaluated for the traits described in Example 5. Selection was also exercised for the purple hulled trait. Thus, all selected lines were homozygous for the purple hulled trait. The $F_4$ lines are bulked to form a purple hulled open pollinated hybrid grown in isolation to yield plants and seed that closely match the $F_1$ hybrid for seed yield and agronomic appearance.

Example 8

In the previous examples presented herein, the described selection of an open pollinated hybrid has been accomplished by matching it with the $F_1$ hybrid from which it was derived. This is a useful selection technique, but it is not essential in the application of this technique and not all products (open pollinated hybrids) developed through the application of this technique will match an existing $F_1$ hybrid. One goal of the present invention is to produce $F_3$ to $F_5$ lines in which the heterosis found in hybrids is fixed and to increase those lines as open pollinated hybrids which can be easily and inexpensively self propagated as a source of true breeding planting seed for the farmer. Once familiar with this technique, the necessity of matching to the initial $F_1$ hybrid is largely eliminated because the breeder learns what a good hybrid should look like and what important traits are needed for seed production within a particular maturity class (early to late hybrids predicated on the timing of flowering and dry down). For example, if a hybrid cross is made to produce a 105-day corn hybrid with an optimum yield potential of 200 bushels per acre, then what is desired is an open pollinated hybrid that will do the same. Thus, as the hybrid cross is advanced through the succeeding generations ($F_2$, $F_3$, $F_4$, etc.) selection of plants can be based on criteria such as 105-day maturity, a good standing variety with suitable resistance to prevalent disease, production of good quality (high test weight seed) and most importantly seed yield in the 200 bushels per acre range. This last parameter is the most important and can be easily estimated on a plant basis. For example, if the plant rate is 26,000 plants per acre in the evaluation plot (a common planting rate for high yield 105-day corn hybrids) and a self pollinated plant is selected with a yield of 7.2 ounces (0.45 lb) of seed, then the yield on a per acre basis would be:

26,000 plants per acre×0.45 pounds per plant=11,700 pounds per acre. 11,700 pounds per acre×56 pounds per bushel=209 bushels per acre.

Obviously, such a plant selection would be a promising candidate as an open pollinated hybrid regardless if it closely matches the $F_1$ hybrid from which it is derived. In actual practice, the selfing process itself can reduce yield since tassels and silks are bagged and silks often receive just one shot of pollen under an ear bag. This is a restrictive, unnatural process. Thus, a selfed plant selection with a yield of 70% to 80% of target yield is a promising open pollinated hybrid candidate since yield under open pollinated conditions are substantially higher.

In oil seed, sunflower optimum hybrid yields are in the 2,000 pounds per acre range. Thus, a good open pollinated hybrid must yield in this optimum yield range. For example, if an $F_3$ plant with a suitable maturity (bloom date and dry down rate), good standability, disease resistance, seed quality yields 1/10th of a pound at a plant rate of 20,000 plants per acre (a common planting rate for commercial oil seed sunflower production fields) then the yield rate per acre would be: 20,000 plants per acre×1/10 of a pound per plant=2,000 pounds per acre. This plant would be an excellent prospect for increase and use as an open pollinated hybrid regardless of how it would match up with the $F_1$ hybrid from which it is derived. Selfed sunflower heads are bagged and generally will yield more when allowed to open pollinate in seed production or commercial grain production fields. Thus, the purpose of this invention is the fixing of the heterosis characteristic in $F_3$, $F_4$, etc. lines that can be increased in isolation to yield open pollinated hybrids. These open pollinated hybrids can be evaluated directly against the $F_1$ hybrid from which they are derived, other commercial quality $F_1$ hybrids from which they were not derived or objective performance parameters (primarily yield) that denote levels of performance indicative of heterotic hybrids.

Thus, one purpose of this invention is to fix the heterosis characteristic in $F_3$, $F_4$ and $F_5$ lines so these lines can be increased in isolation to yield open pollinated hybrids. These open pollinated hybrids can be evaluated directly against the $F_1$ hybrid from which they are derived, other commercial quality $F_1$ hybrids from which they were not derived or objective performance parameters (primarily yield) that denote levels of performance indicative of heterotic hybrids.

To those skilled in the art many variations and modifications on the products and procedures described in this invention will become obvious without departing from the true spirit and intent of the invention.

Jack F. Carter, Editor: *Sunflower Science and Technology*, 1978. American Society of Agronomy Publishers, Inc., Madison, Wis., USA.

J. T. Gerdes et al., *Compilation of North American Maize Breeding Germplasm*, 1994. Crop Science Society of America Inc., Madison, Wis., USA.

Anon. *Seedsman's Hand Book*, 8th Edition, 1981. Mike Brayton Seeds, Inc., Ames, Iowa, USA.

Anon. *Seedsman's Handbook*, 16th Edition, 1989. MBS, Inc., Ames, Iowa, USA.

G. E. Sprague, Editor: *Corn and Corn Improvement*, 1977. American Society of Agronomy Publishers Inc., Madison, Wis., USA.

H. K. Hayes, *A Professors Story of Hybrid Corn*, 1963. Burgess Publishing Company, Minneapolis, Minn., USA.

A. R. Crabb, *The Hybrid-Corn Makers: Prophets of Plenty*, 1947. Rutgers University Press, New Brunswick, N.J., USA.

H. A. Wallace and W. L. Brown, *Corn and Its Early Fathers* (Revised edition) 1988. Iowa State University Press, Ames, Iowa, USA.

R. W. Allard, *Principles of Plant Breeding*, 1960. John Wiley and Sons Inc., New York, N.Y., USA

What is claimed is:

1. A method of producing corn hybrids comprising:
   a) crossing a Reid Yellow Dent Stiff Stalk Synthetic (SSS) derived line and a Lancaster Surecrops (C103) derived line to produce an initial $F_1$ hybrid;
   b) selfing said $F_1$ hybrid to produce $F_2$ seed;
   c) growing $F_2$ plants and selfing those plants that have the same height, maturity, and ear size as the $F_1$ hybrid;
   d) selecting the selfed $F_2$ ears with $F_3$ seed that have a grain yield that is at least 90% of the $F_1$ hybrid;
   e) growing $F_3$ plants from selected $F_2$ ears;
   f) selfing $F_3$ plants that have the same height, maturity, and ear size as the $F_1$ hybrid;
   g) selecting the selfed $F_3$ ears with $F_4$ seed that have a grain yield that is at least 90% of the $F_1$ hybrid;
   h) growing $F_4$ plants from selected $F_3$ ears;
   i) selfing $F_4$ plants that have the same height, maturity, and ear size as the $F_1$ hybrid;
   j) selecting the selfed $F_4$ ears with $F_5$ seed that have a grain yield that is at least 90% of the $F_1$ hybrid;
   k) growing the $F_5$ seed from a single selected $F_4$ plant in field isolation to produce an open pollinated corn hybrid.

2. The Method of claim 1 in which the $F_4$ seed from a single selected $F_3$ plant is grown in field isolation to produce an open pollinated corn hybrid.

3. The Method of claim 1 in which the $F_3$ seed from a single selected $F_2$ plant is grown in field isolation to produce an open pollinated corn hybrid.

4. The Method of claim 1 in which the $F_6$ seed from a single selected $F_5$ plant is grown in field isolation to produce an open pollinated corn hybrid.

5. The Method of claim 1 in which any selfing generation seed from a single selected plant beyond the $F_5$ is grown in field isolation to produce an open pollinated corn hybrid.

6. The Method of claim 1 wherein said complementary heterotic corn lines are selected from the group consisting of inbreds or single cross hybrids.

7. The open-pollinated corn hybrid described in claim 1.
8. The open-pollinated corn hybrid described in claim 2.
9. The open-pollinated corn hybrid described in claim 3.
10. The open-pollinated corn hybrid described in claim 4.
11. The open-pollinated corn hybrid described in claim 5.
12. A method of producing sunflower hybrids comprising:
   a) crossing a Peredovick derived CMS line and a Wild Sunflower derived Restorer line to produce an initial $F_1$ hybrid;
   b) selfing said $F_1$ hybrid to produce $F_2$ seed;
   c) growing $F_2$ plants and selfing those plants that have the same height, maturity, and head size as the $F_1$ hybrid;
   d) selecting the selfed $F_2$ heads with $F_3$ seed that have a grain yield that is at least 90% of the $F_1$ hybrid;
   e) growing $F_3$ plants from selected $F_2$ heads;
   f) selfing $F_3$ plants that have the same height, maturity, and head size as the $F_1$ hybrid;
   g) selecting the selfed $F_3$ heads with $F_4$ seed that have a grain yield that is at least 90% of the $F_1$ hybrid;
   h) growing $F_4$ plants from selected $F_3$ heads;
   i) selfing $F_4$ plants that have the same height, maturity, and head size as the $F_1$ hybrid;

j) selecting the selfed $F_4$ heads with $F_5$ seed that have a grain yield that is at least 90% of the $F_1$ hybrid;

k) growing the $F_5$ seed from a single selected $F_4$ plant in field isolation to produce an open pollinated sunflower hybrid.

13. The Method of claim 12 in which the $F_4$ seed from a single selected $F_3$ plant is grown in field isolation to produce an open pollinated sunflower hybrid.

14. The Method of claim 12 in which the $F_3$ seed from a single selected $F_2$ plant is grown in field isolation to produce an open pollinated sunflower hybrid.

15. The Method of claim 12 in which the $F_6$ seed from a single selected $F_5$ plant is grown in field isolation to produce an open pollinated sunflower hybrid.

16. The Method of claim 12 in which any selfing generation seed from a single selected plant beyond the $F_5$ is grown in field isolation to produce an open pollinated sunflower hybrid.

17. The Method of claim 12 wherein said complementary heterotic sunflower lines are selected from the group consisting of inbreds or single cross hybrids.

18. The open-pollinated sunflower hybrid described in claim 12.

19. The open-pollinated sunflower hybrid described in claim 13.

20. The open-pollinated sunflower hybrid described in claim 14.

21. The open-pollinated sunflower hybrid described in claim 15.

22. The open-pollinated sunflower hybrid described in claim 16.

23. The method of claim 1 in which a Reid Yellow Dent Stiff Stalk Synthetic (SSS) derived line is crossed with a Canadian Morden (CMV3) derived line to produce an initial $F_1$ hybrid.

24. The method of claim 1 in which a Reid Yellow Dent Stiff Stalk Synthetic (SSS) derived line is crossed with an Early Butler (CO109) derived line to produce an initial $F_1$ hybrid.

25. The method of claim 1 in which a Reid Yellow Dent Stiff Stalk Synthetic (SSS) derived line is crossed with a High Yield (HY) derived line to produce an initial $F_1$ hybrid.

26. The method of claim 1 in which a Reid Yellow Dent Stiff Stalk Synthetic (SSS) derived line is crossed with an Ohio 43 (OH43) derived line to produce an initial $F_1$ hybrid.

27. The method of claim 1 in which a Reid Yellow Dent Stiff Stalk Synthetic (SSS) derived line is crossed with a Wisconsin 153 (W153) derived line to produce an initial $F_1$ hybrid.

28. The method of claim 1 in which a Reid Yellow Dent Stiff Stalk Synthetic (SSS) derived line is crossed with a Wilson Farm Reid (WF9) derived line to produce an initial $F_1$ hybrid.

* * * * *